US012588931B2

(12) United States Patent
Hafez et al.

(10) Patent No.: US 12,588,931 B2
(45) Date of Patent: Mar. 31, 2026

(54) METHOD AND TOOL FOR MEASURING AND CORRECTING DEFORMITIES FOR FRACTURES AND OSTEOTOMIES

(71) Applicant: Mahmoud Alm El Din Hafez, Giza (EG)

(72) Inventors: Mahmoud Alm El Din Hafez, Giza (EG); Mansoor Tahnoon Al Nehayan, Al Ain (AE)

(73) Assignee: Mahmoud Hafez, Giza (EG)

( * ) Notice: Subject to any disclaimer, the term of this patent is extended or adjusted under 35 U.S.C. 154(b) by 271 days.

(21) Appl. No.: 18/281,453

(22) PCT Filed: Mar. 14, 2021

(86) PCT No.: PCT/EG2021/000007
§ 371 (c)(1),
(2) Date: Sep. 11, 2023

(87) PCT Pub. No.: WO2022/194335
PCT Pub. Date: Sep. 22, 2022

(65) Prior Publication Data
US 2024/0164812 A1 May 23, 2024

(51) Int. Cl.
A61B 17/62 (2006.01)
A61B 17/00 (2006.01)
(Continued)

(52) U.S. Cl.
CPC .............. A61B 17/62 (2013.01); A61B 17/66 (2013.01); A61B 90/06 (2016.02);
(Continued)

(58) Field of Classification Search
CPC ......... A61B 17/62; A61B 17/66; A61B 90/06; A61B 2017/0092; A61B 2017/00982; A61B 2017/606
See application file for complete search history.

(56) References Cited

U.S. PATENT DOCUMENTS 5,207,676 A * 5/1993 Canadell ............ A61B 17/6491
606/57
5,728,095 A 3/1998 Taylor
(Continued)

FOREIGN PATENT DOCUMENTS

CN 108742804 A 11/2018
EP 0177270 A2 4/1986
SU 1132934 A1 1/1985

*Primary Examiner* — Nicholas J Plionis
(74) *Attorney, Agent, or Firm* — Dickinson Wright PLLC; Andrew D. Dorisio

(57) ABSTRACT

This invention is a method and tool for measuring and correcting deformities during osteotomy and treatment of fractures. The tool designed to restoring, alignment and correcting deformities of bone and joints is based on preoperative imaging and calculation of the deformity angle and planning for the deformity correction, the tool has a mechanism and power to force the bone to move according to the planning trajectory aiming at normal alignment during osteotomy and treatment of fracture and dislocation, it has a gauge to measure the degree of correction and the value of the bone displacement needed to overcome the bone overlapping and deformity angle in the fracture zone.

13 Claims, 10 Drawing Sheets

(51) Int. Cl.

| | | |
|---|---|---|
| *A61B 17/60* | (2006.01) | |
| *A61B 17/66* | (2006.01) | |
| *A61B 90/00* | (2016.01) | |

(52) U.S. Cl.
CPC ................. *A61B 2017/0092* (2013.01); *A61B 2017/00982* (2013.01); *A61B 2017/606* (2013.01)

(56) References Cited

U.S. PATENT DOCUMENTS

| | | | |
|---|---|---|---|
| 2003/0069580 A1* | 4/2003 | Langmaid | A61B 17/6416 |
| | | | 606/59 |
| 2009/0177198 A1* | 7/2009 | Theodoros | A61B 17/62 |
| | | | 606/56 |
| 2014/0336648 A1 | 11/2014 | Van Aaken | |
| 2018/0221034 A1* | 8/2018 | Struik | A61B 17/66 |
| 2019/0231393 A1* | 8/2019 | Riccione | A61B 17/62 |
| 2019/0336171 A1* | 11/2019 | Lavi | A61B 34/10 |
| 2021/0212729 A1* | 7/2021 | Sun | A61B 17/6475 |

* cited by examiner

Figure:   1
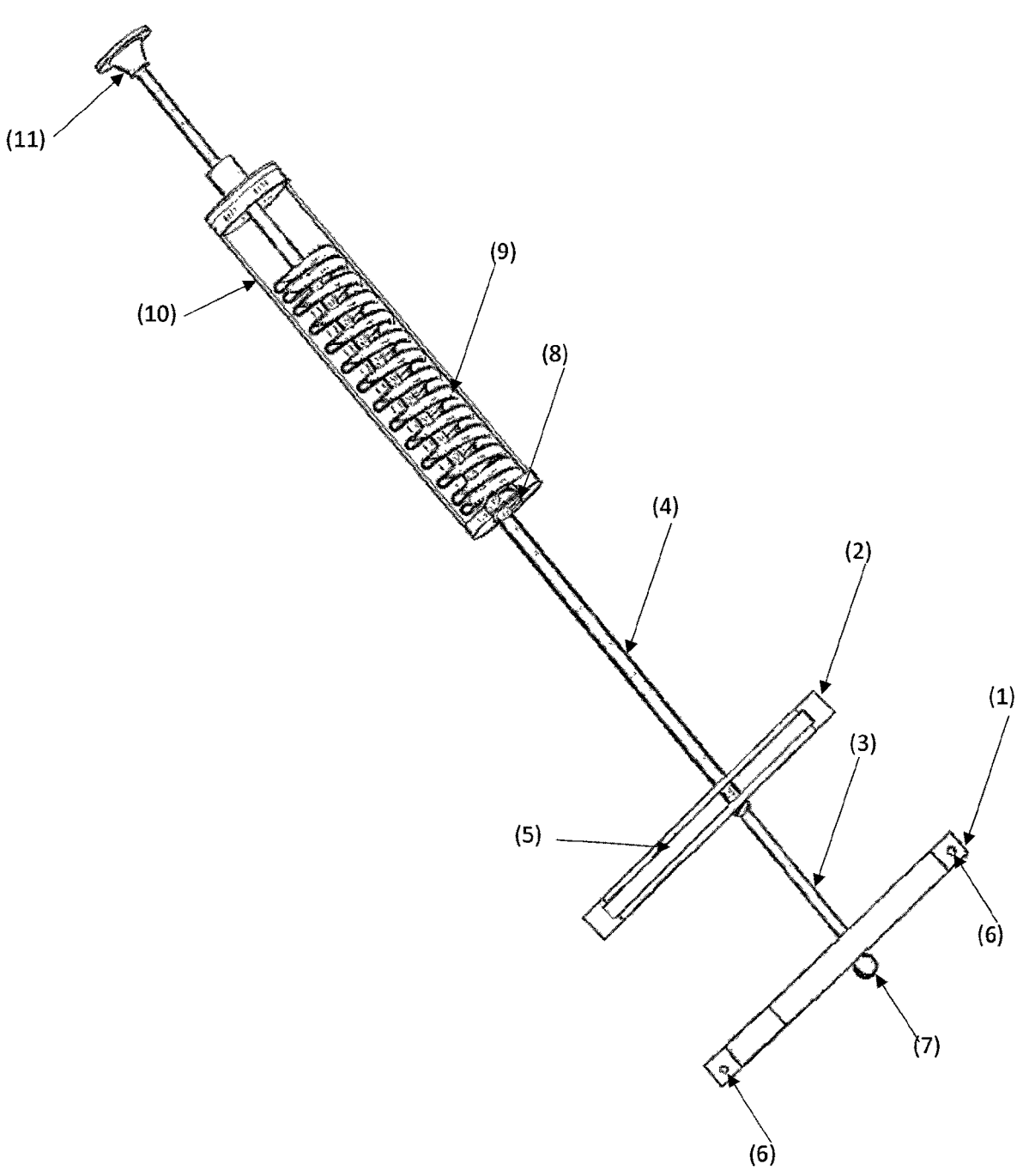

Figure: 2
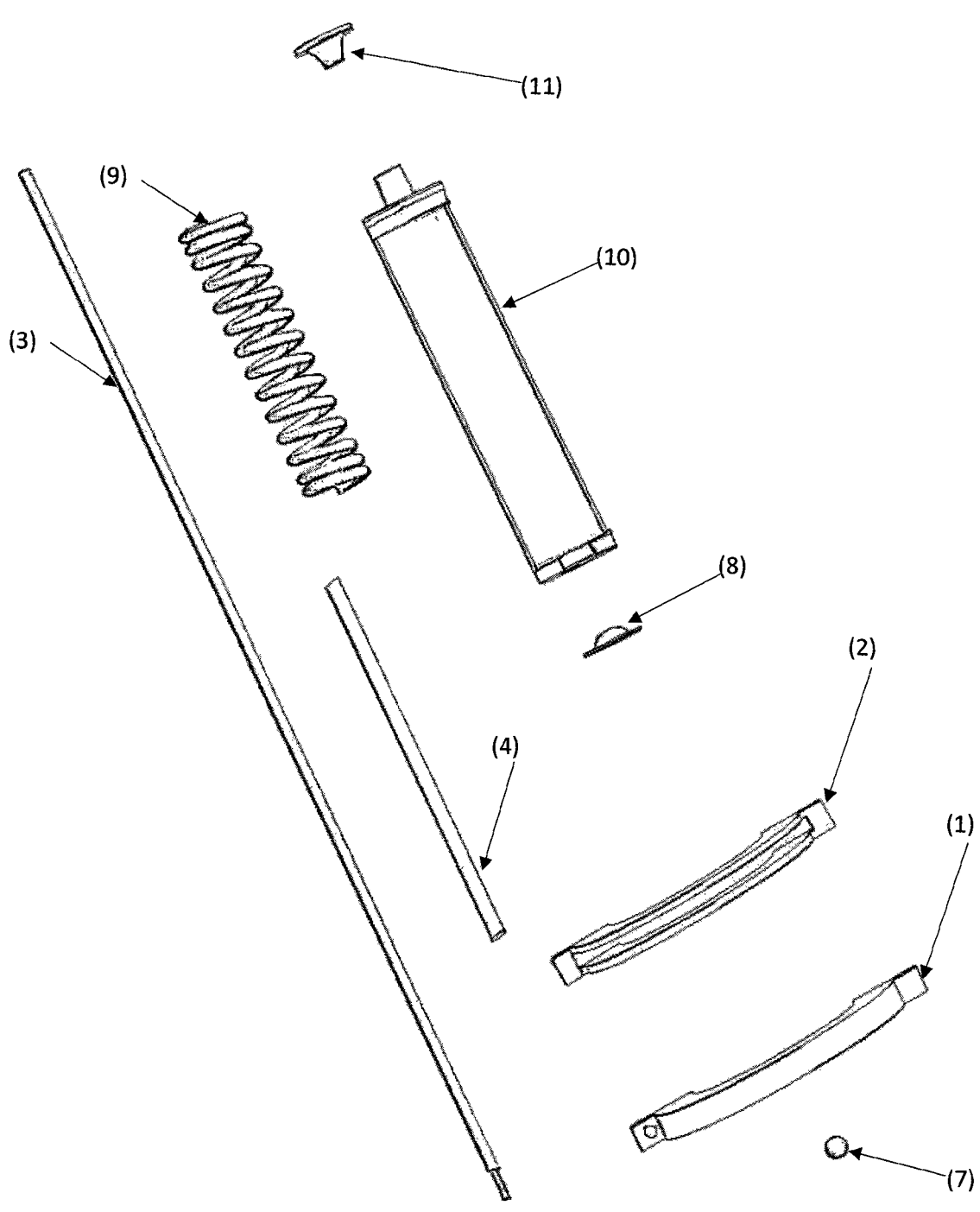

Figure:  3
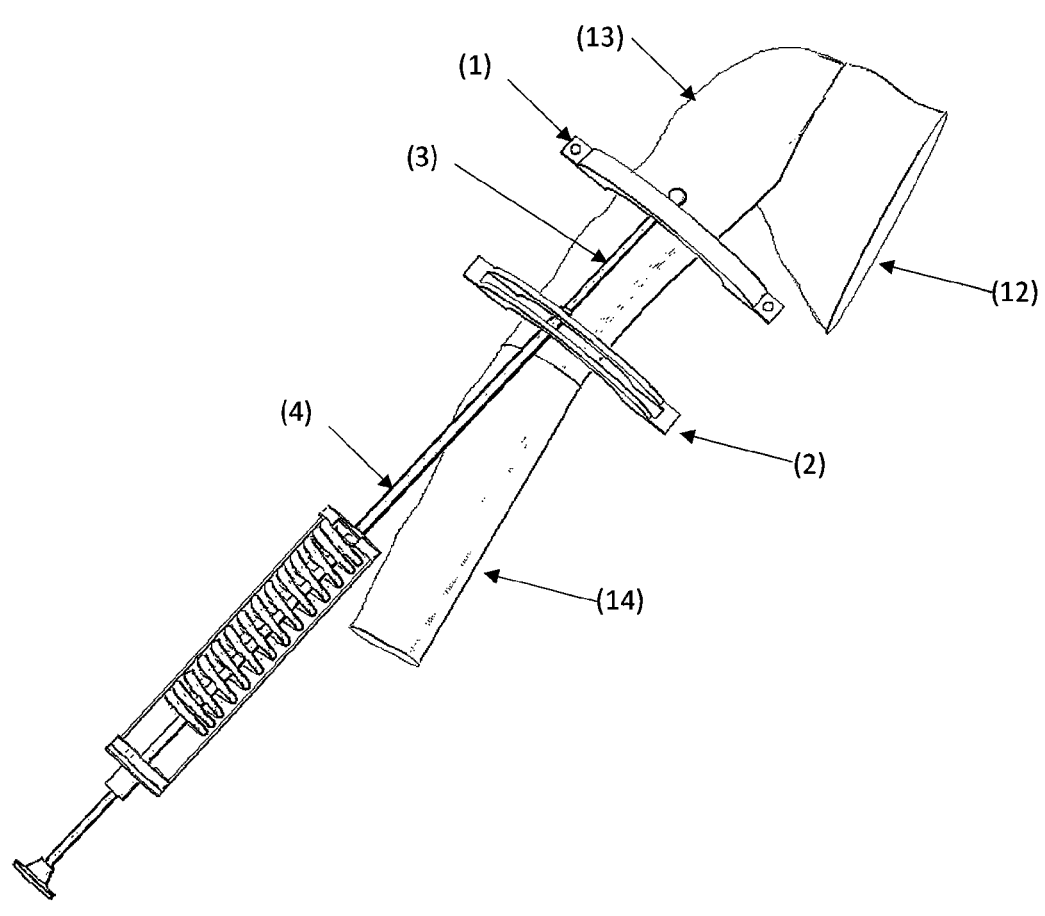

Figure: 4
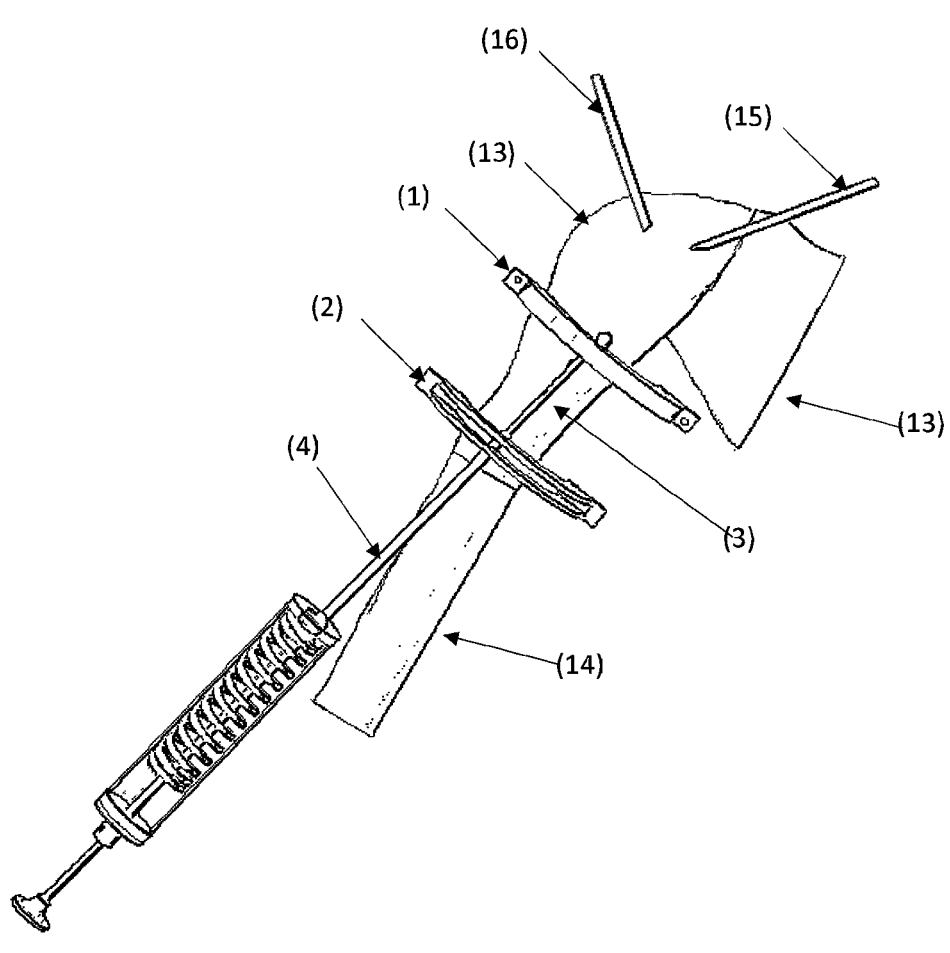

Figure:  5
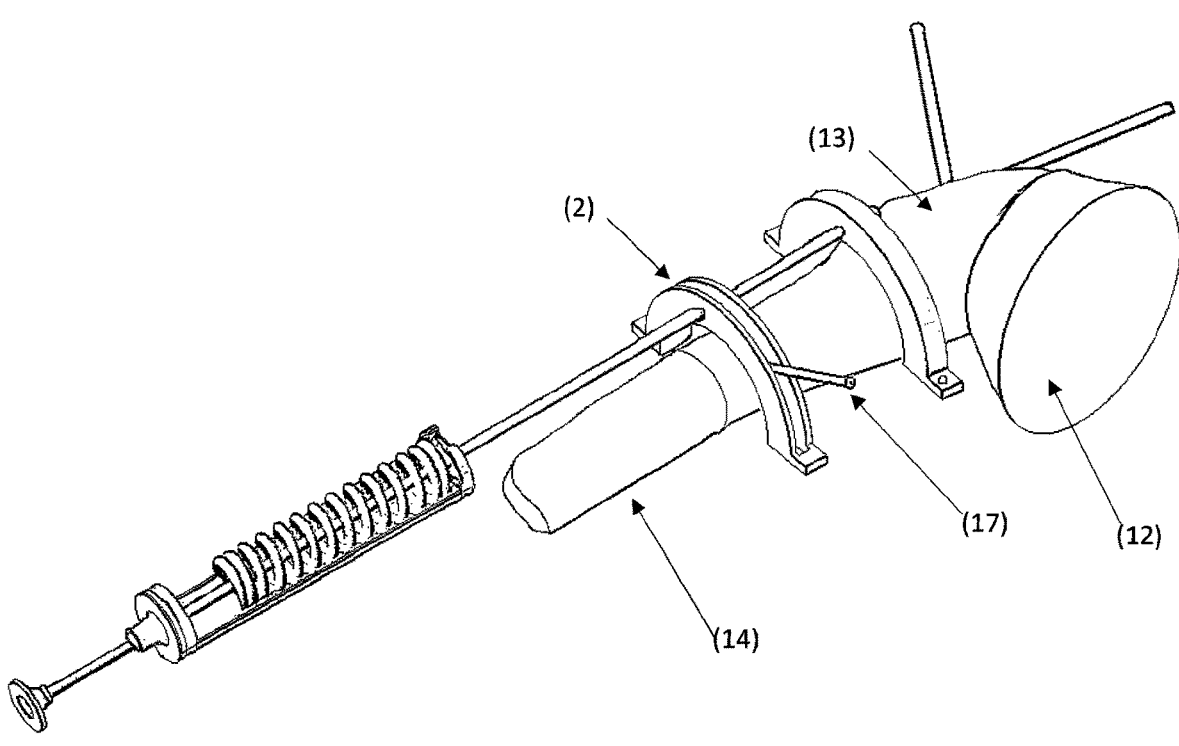

Figure:   6
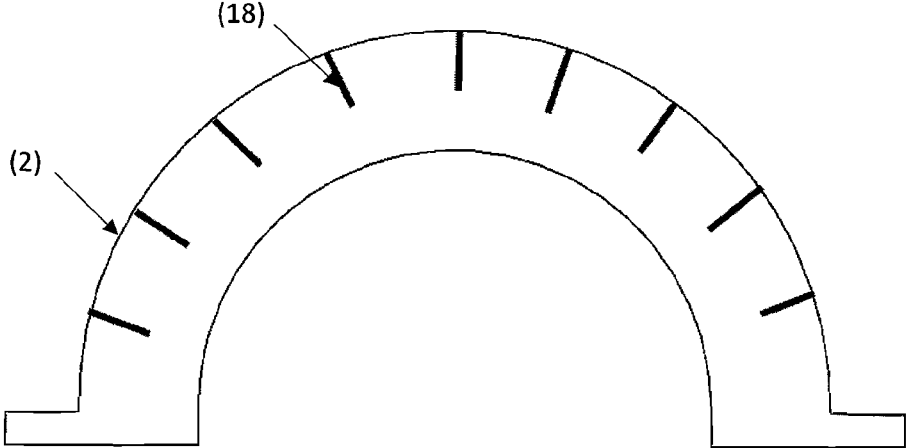

Figure:  7
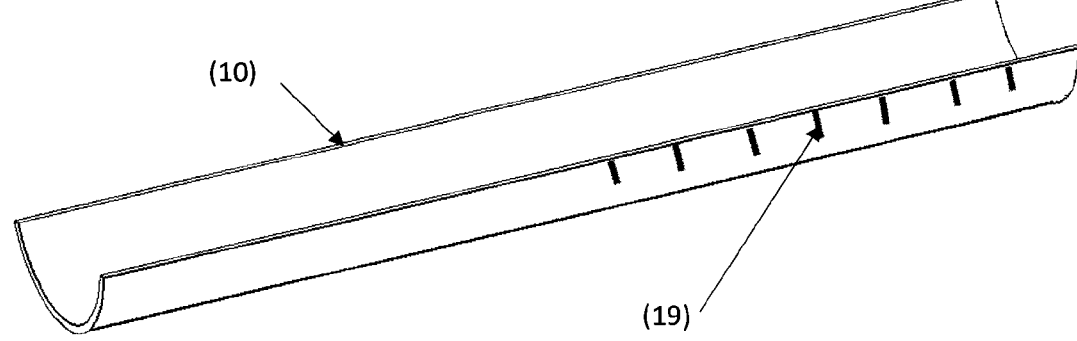

Figure: 8
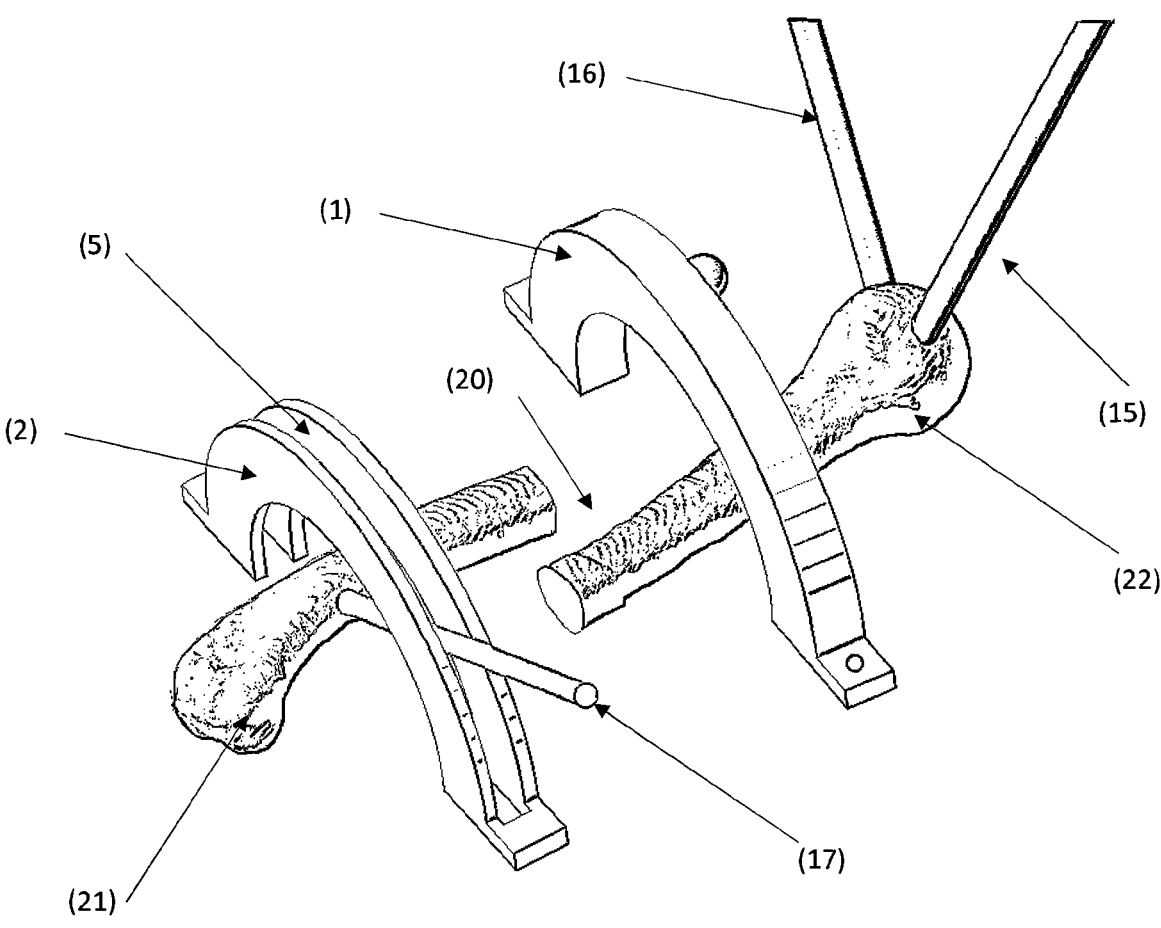

Figure: 9
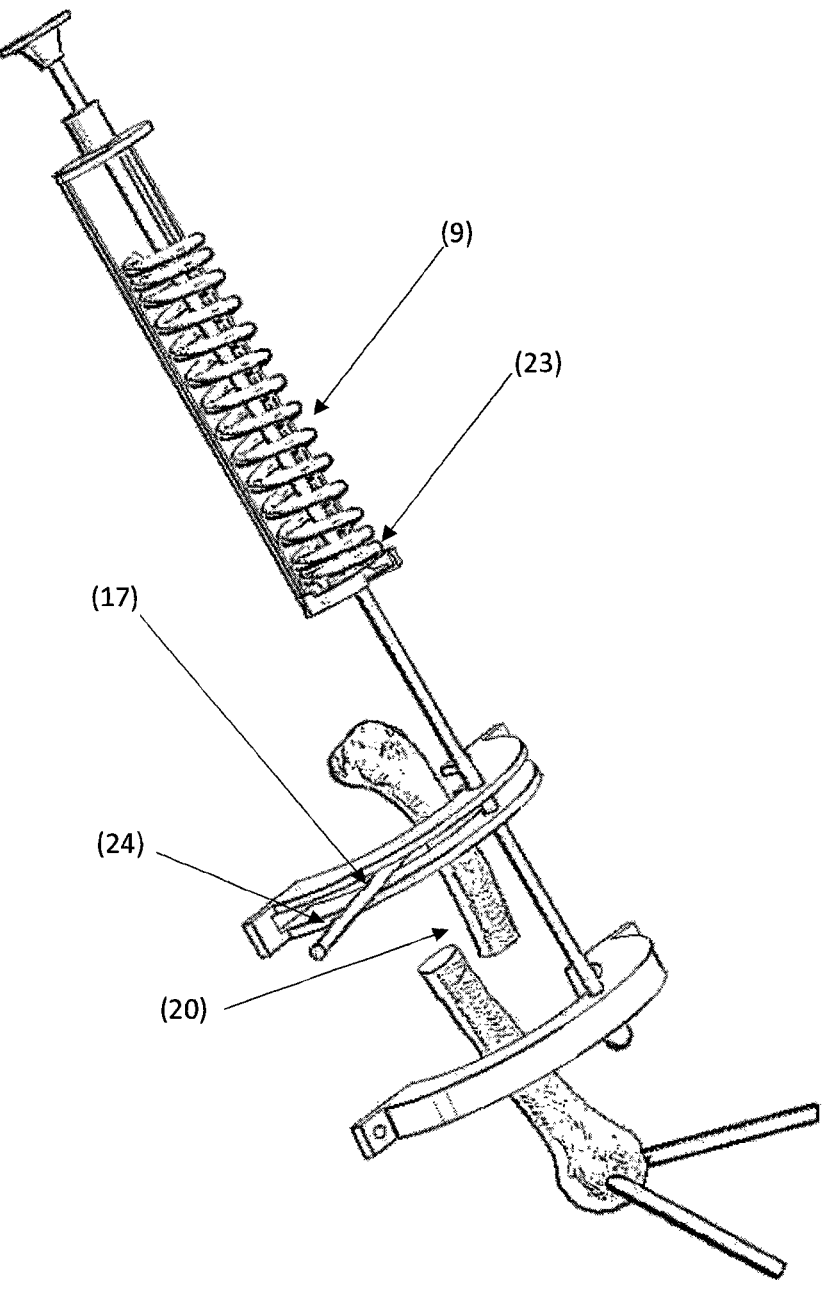

Figure: 10
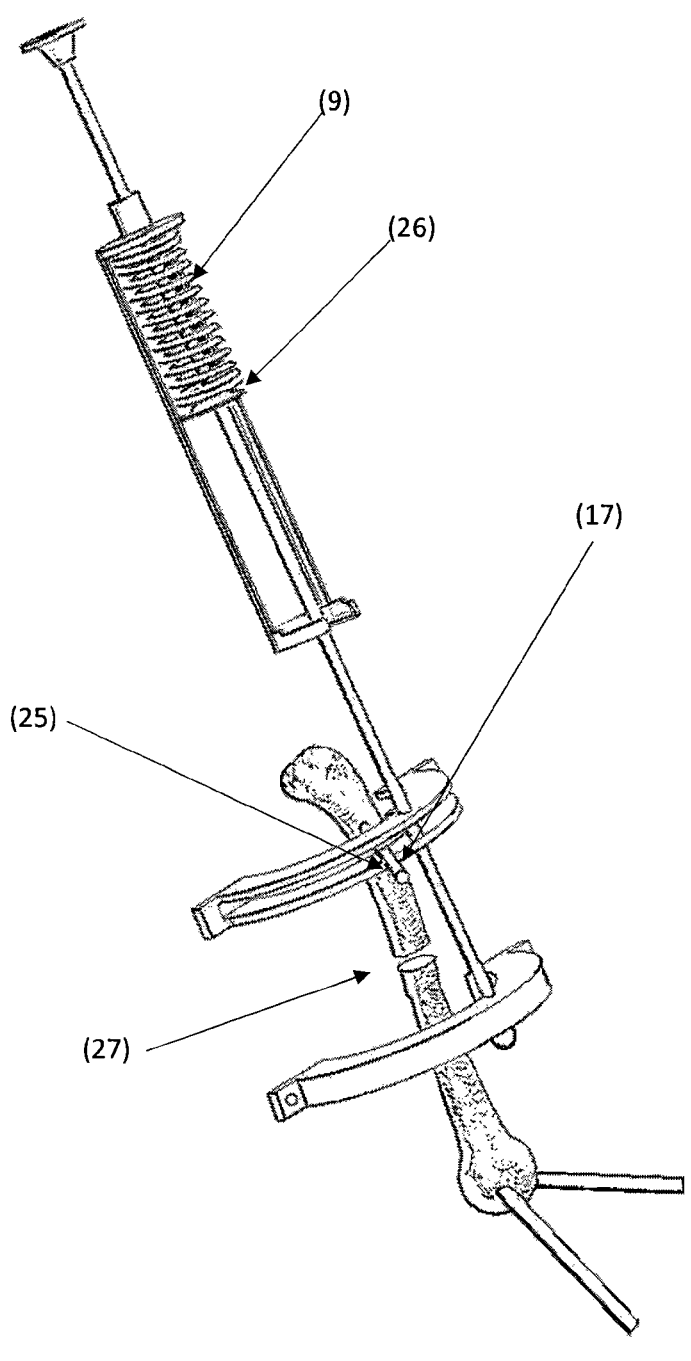

METHOD AND TOOL FOR MEASURING AND CORRECTING DEFORMITIES FOR FRACTURES AND OSTEOTOMIES

TECHNICAL FIELD

A tool used to measure and correct bone overlapping and deformity angle and deformities for a patient who has a bone fracture or is in need of osteotomy correction. The tool is designed and used based on a method of preoperative planning in which the correct angle and displacement required to treat the bone fracture and/or deformity is based on CT scan.

BACKGROUND OF THE SUBJECT

Fractures of bones and dislocations of joints are a common problem and usually difficult to treat. Most of the time the fractures are displaced and all dislocations are already displaced. The cause of displacement is the pull of attached muscles towards certain direction. First line of management is to reduce the displacement and the second line is to fix it in the reduced position to prevent further displacement. The reduction could be closed that means without opening the skin and soft tissue or could be an invasive open reduction with cutting skin and soft tissue to reach the displaced bone or the joint. Also, the fixation could be closed or open. Occasionally, the reduction could be closed while the fixation is open. In most of these procedures, sedation or full anesthesia is required to eliminate pain and relax muscle resistance.

There are a surgical procedure called osteotomy which is a cut in the bone to allow a change in its position such as correction of a deformity, shortening or lengthening the bone. This artificial scenario is similar to fractures and require the same management that is reduction and fixation.

CURRENT ART

The tradition methods for reducing displacement of fractures and dislocations are the traction. There are several ways to achieve traction during operative or non operative management. It can be achieved by manual pull with counter traction. Skin traction with a weight at the other end to provide continuous pull at the distal end of the bone. Skeletal traction is another method, where a pin is inserted in the distal part of the bone or the limb attached to stirrup that is pulled by heavy weight. A fracture table is method to achieve reduction during surgery. Different tools are used to help in reduction during surgery such as external fixator or Ilizarov techniques to provide continuous and gradual traction or distraction to the bone.

Novel techniques such as AO traction redactor, rapid reductor and traction repositor were recently introduced.

All these methods have their own limitations. There is usually inconsistency between muscle pull and the direction of the traction force. The force exerted by these methods cannot be accurately measured and has limited force. Traction cannot be used for distal fractures or for amputated limbs. Traction tables are bulky, not easily portable and expensive.

These methods are associated with risk of complications, such as neurologic (stretch injury of the foot, pudendal nerve trauma, peroneal nerve palsy) and soft tissue injuries (perineal ulcers), and compartment syndrome.

DESCRIPTION OF INVENTION

The invention is a method based on software assistance on determining direction and degree of deformities combining with a special designed tool to perform the surgery to correct deformities for osteotomies and fractures. The first step is reconstructing a 3D model of the patient bone based on the captured 2D images of the CT-Scan, then the on a specific software a preoperative planning will be applied to detect the correct displacement of the fractured bone to overcome the bone overlapping and deformity angle due fracture and also detect the correct rotation angle between the two parts of the fractured bone.

After determine the correct degree and direction of deformities, the software designs a way for correcting the deformities of the osteotomy and the reduction of displaced fractures by detecting the trajectory line for osteotomy in the form of one single cut to correct multi planes deformities.

Based on the presented method a tool designed to perform the bone reduction and correct the deformities for osteotomy and bone fractures. The tool consisting of fixed proximal ring (1), movable distal ring (2), alignment rod (3), sleeve (4), fixation holes (6), fixation sphere (7), front rubber (8), spring (9), holder (10), back rubber (11) and rotation correction arm (17). Two accessory rods (the medial fixation rod (15) and the lateral fixation rod (16)) are added to tool assembly during surgery for the purpose of bone fixation. See FIGS. 1, 2 and 4)

The tool used in correcting the bone and joints fractions and deformities is designed to be based on image guided surgery for bone and joint. The tool used in such surgery for bones and joints fractions and deformities should have a source of mechanical o electrical power to generate a high force to be able to resist the hard structure of the joints and bones as well as a hard mechanical design for the bone reduction and the correction of deformities that acquires a high force to perform such process in order to generate a high torque. The tool must have a mechanical system providing a reasonable source power like springs and/or threads, the mechanical system could be replaced by an electrical system to generate an electrical power to control the motion and rotation of the tool component.

For a precise surgery, high accuracy measurements for the fractions and deformities must be taken very acutely so that the software gather all the information needed to design the a trajectory line for osteotomy in the form of one single cut and removes the excessed fractions and deformities. Such a tool must be designed in a way to be sanitized easily without any losses such as abrasion or erosion and withstand high temperature and harsh sanitization liquids such as the heat of autoclave during sterilization, so the tool is manufactured from like stainless steel 316, stainless steel 314, titanium and/or nylon PA12 that tolerates wide ranges of heat of autoclave during sterilization process.

To perform accurate measurements and true acknowledgments of the fractions and deformities values of the bones and joint.

Gauges (FIGS. 6 and 7) must be attached to the tool in order to measure the degree of correction and reduction of bone, these values are important data needed to provide the surgeon by the correct values of the trajectory line for osteotomy in the form of one single cut to correct multiplanes deformities. The surgery is performed in error-free manner.

Since the tool is based on image guided surgery, for bone and joints such as CT-scan, X-ray, MRI and/or ultrasound as a main feature for the tool that creates the vision factor of the surgery. So the tool is manufactured from radiolucent material so that it does not interfere with the use of intraoperative x-ray.

The outcomes of the preoperative planning process are the values of bone displacement and bone rotation, which will be recorded on the tool gauges (FIGS. 6 and 7) to guide the surgeon to perform the correction surgery by knowing the correct values for bone displacement and bone rotation before the surgery and without needing of big skin incision because the tool fixation over the fractured bone is minimally invasive.

To perform the surgery, the surgeon should use the two accessory rods (the medial fixation rod (15) and the lateral fixation rod (16)) to fix the proximal part of the fractured bone and prevent it from motion and rotation at any directions. As example in FIG. 4, the figure shows the two accessory rods fix the upper arm at the proximal area. For clarification, FIG. 8 shows the naked fractured bone that was fixed in the proximal part by using the two accessory fixation rods in both side laterally and medially. The two accessory fixation rods enter the proximal part of the bone through and over the skin in percutaneous way.

The tool component will be assembled and fixed over the upper arm during the surgery as shown in the FIG. 4. The fixed proximal ring (1) seated on the upper arm in the proximal area and will be fixed in the surgery table by two fixation screws through the fixation holes (6), the movable distal ring (2) seated on the upper arm in the distal area.

The alignment rod (3) will be putted inside the sleeve (4) and pass through the movable distal ring (2), the front rubber (8), spring (9), and back rubber (11). The tip alignment rod (3) will be fix in the fixed proximal ring (1) by using the fixation sphere (7). See FIGS. 1, 2 and 4).

The sleeve (4) should be fixed in the movable distal ring (2) and the front rubber (8).

The rotation correction arm (17) will be inserted in the distal part of the bone the skin and will guided and controlled by the rotation correction slot (5). See FIGS. 1, 2 and 5).

By assembling the tool component as mentioned, the surgeon will be able to perform the surgery by knowing the values of required bone displacement and bone rotation as it comes from the preoperative planning process. The system now in original position all the spring tip (9) and the rotation correction arm (17) in their zero position before correction. FIG. 9 shows focused anatomy view of the positioning of the tool over the humerus bone, the figures shows the naked bone and presents the overlapping and deformity angle between the two parts of the fractured bone in the fracture zone (20). It also shows the original (zero) position of the rotation correction arm (17) and the tip of spring (9) in its original position (23).

The surgeon will pull the back rubber (11) which compress the spring and pull the sleeve (4), movable distal ring (2) and rotation correction arm (17) to their final correct position (26). The moving of movable distal ring (2) and rotation correction arm (17) will lead to free the bone in the fracture zone (20) from the overlapping and deformity angle problem and return the both parts of the fractured bone to their original and anatomical axis (FIG. 10, label 27). See FIGS. (5, 8, 9 and 10).

Final correct position (26) is known from the preoperative planning, final correct position (26) is the required value of the bone displacement to overcome the bone over lapping in the fracture zone (20). The side wall of the holder (10) as shown in FIG. 7) has a gauge or scale (19) to allow the surgeon to stop the spring at the correct distance as planned in the preoperative planning process. The gauge is designed in centimeter scale which is reasonable in this kind of surgeries.

The last step in this surgery is correcting the rotation angle of the both parts of the fractured bone. To perform this step, the surgeon should rotate the rotation correction arm (17) to its final correct position (25) which is known from the preoperative planning process. The wall of the movable distal ring (2) as shown in FIG. 6) has a gauge or scale (18) to allow the surgeon to rotate the rotation correction arm (17) to its correct angle as planned in the preoperative planning process. The gauge is designed in radian degree scale which is reasonable in this kind of surgeries. As the rotation correction arm (17) is inserted in the distal part of the bone, that is mean the distal part will also rotate by the same correct rotation degree to return the distal part of the fractured bone to its original and anatomical axis, (FIG. 10, label 27).

By applying these two steps o bone displacement and bone rotation, it will treat and overcome the overlapping and deformity angle of the bone in the fracture zone.

This method and tool is applicable to restoring, alignment and correcting deformities of bone and joints in all human body.

DRAWINGS DESCRIPTION

FIG. 1: The figure shows the assembly of the tool. The fixed proximal ring (1), the movable distal ring (2), the alignment rod (3), sleeve (4), rotation correction slot (5), fixation holes (6), fixation sphere (7), front rubber (8), spring (9), holder (10) and back rubber (11).

FIG. 2: The figure shows the component of the tool. The fixed proximal ring (1), the movable distal ring (2), the alignment rod (3), sleeve (4), fixation holes (6), fixation sphere (7), front rubber (8), spring (9), holder (10) and back rubber (11).

FIG. 3: The figure shows the positioning of the tool over the arm. The upper arm (13), shoulder (12), forearm (14), The fixed proximal ring (1), the movable distal ring (2), the alignment rod (3) and sleeve (4).

FIG. 4: The figure shows the positioning of the tool over the arm and the positions the fixations rods. The upper arm (13), shoulder (12), forearm (14), The fixed proximal ring (1), the movable distal ring (2), the alignment rod (3), sleeve (4), the medial fixation rod (15) and the lateral fixation rod (16).

FIG. 5: The figure shows the positioning of the tool over the arm, the positions the fixations rods and the position of the rotation correction arm. The upper arm (13), shoulder (12), forearm (14), the movable distal ring (2), the medial fixation rod (15), the lateral fixation rod (16) and the rotation correction arm (17).

FIG. 6: The figure shows rotation angle scale (18) on the movable distal ring (2)

FIG. 7: The figure shows displacement scale (19) on the movable distal ring (10)

FIG. 8: The figure shows focused anatomy view of the positioning of the tool over the humerus bone in the facture zone. The proximal humerus bone (22), The distal humerus bone (21), the fracture zone (20), the medial fixation rod (15), the lateral fixation rod (16), The fixed proximal ring (1), the movable distal ring, the movable distal ring (2), the rotation correction slot (5), and the rotation correction arm (17).

FIG. 9: The figure shows focused anatomy view of the positioning of the tool over the humerus bone in the facture zone in original position before correction. The fracture zone (20), the rotation correction arm (17) in its original position (24), the tip of spring (9) in its original position (23).

FIG. 10: The figure shows focused anatomy view of the position of the tool over the humerus bone in the facture zone in after correction. The corrected fracture zone (27), the rotation correction arm (17) in its final correct angle position (25), the tip of spring (9) in its final correct displacement position (26).

The invention claimed is:

1. A tool for restoring alignment and correcting deformities of bones and joints based on preoperative imaging and calculation of the deformity angle and planning for the deformity correction, the tool comprising a fixed proximal ring (1), a movable distal ring (2), a tip alignment rod (3), a sleeve (4), fixation holes (6), a fixation sphere (7), a front rubber (8), a spring (9), a holder (10), a back rubber (11) and a rotation correction arm (17);

wherein the sleeve is fixed to the movable distal ring and the front rubber;

wherein the front rubber and the back rubber are disposed on opposite sides of the spring on the tip alignment rod adapted to provide traction; and wherein the tool is adapted for forcing the bone to move according to a planning trajectory aiming at normal alignment during osteotomy and treatment of fracture and dislocation, and further includes a first gauge (18) to measure a degree of correction and a value of the bone displacement needed to overcome bone overlapping and deformity angle in a fracture zone.

2. The tool according to claim 1, further including a medial fixation rod (15) and a lateral fixation rod (16) adapted to fix and prevent a proximal part of the fractured bone from moving and rotating in any direction.

3. The tool according to claim 1, wherein the tip alignment rod (3) is fixed to the fixed proximal ring (1) by the fixation sphere (7).

4. The tool according to claim 1, wherein a side wall of the holder (10) includes a second gauge (19) adapted to stop the spring (9) at a predetermined distance based on the preoperative planning process.

5. The tool according to claim 1, wherein a wall of the movable distal ring (2) includes the gauge (18) to allow the surgeon to rotate the rotation correction arm (17) to its correct angle as planned in the preoperative planning process.

6. The tool according to claim 1, wherein the spring (9) includes compressed power to pull the distal part of the fracture bone.

7. The tool according to claim 1, wherein the rotation correction arm (17) is adapted to rotate the distal part of the fracture bone to a desired anatomical position according to the planned value based on the preoperative planning method and by using the gauge (18), which is provided on the movable distal ring (2).

8. The tool according to claim 1, comprising a radiolucent material so that the tool does not interfere with the use of intraoperative x-ray.

9. The tool according to claim 1, comprising a material that tolerates the heat of an autoclave during sterilization.

10. The tool according to claim 1, further including a mechanical or electrical power source to force the bone reduction and the correction of deformities.

11. A tool for restoring alignment and correcting deformities of bones and joints based on preoperative imaging and calculation of the deformity angle and planning for the deformity correction, the tool comprising a fixed proximal ring (1), a movable distal ring (2), a tip alignment rod (3), a sleeve (4), fixation holes (6), a fixation sphere (7), a front rubber (8), a spring (9), a holder (10), a back rubber (11) and a rotation correction arm (17);

wherein the tool is adapted for forcing the bone to move according to a planning trajectory aiming at normal alignment during osteotomy and treatment of fracture and dislocation, and further includes a first gauge (18) to measure a degree of correction and a value of the bone displacement needed to overcome bone overlapping and deformity angle in a fracture zone;

wherein the rotation correction arm (17) is adapted to rotate a distal part of the bone to a desired anatomical position according to the planned value based on the preoperative planning method and by using the first gauge (18), which is provided on the movable distal ring (2); and wherein the rotation correction arm (17) is adapted to be guided by a rotation correction slot (5) in a wall of the movable distal ring (2).

12. The tool according to claim 11, wherein a side wall of the holder (10) includes a second gauge (19) adapted to stop the spring (9) at a predetermined distance based on the preoperative planning process.

13. The tool according to claim 11, wherein the sleeve is fixed to the movable distal ring and the front rubber, and wherein the front rubber and the back rubber are disposed on opposite sides of the spring on the tip alignment rod adapted to provide traction.

\* \* \* \* \*